United States Patent [19]
Dragan

[11] 3,942,525
[45] Mar. 9, 1976

[54] ATHLETIC WRAP

[76] Inventor: William B. Dragan, R.F.D. No. 1 Burr St., Fairfield, Conn. 06430

[22] Filed: Mar. 10, 1975

[21] Appl. No.: 556,806

[52] U.S. Cl. .......... 128/165; 128/169; 128/DIG. 15; 273/54 B
[51] Int. Cl.² ......................................... A61F 13/00
[58] Field of Search ........... 128/157, 165, 327, 169, 128/170, 171, 77, DIG. 15; 273/54 B, 183 B

[56] References Cited
UNITED STATES PATENTS

| | | | |
|---|---|---|---|
| 3,238,939 | 3/1966 | Stubbs | 128/165 |
| 3,390,680 | 7/1968 | Marcum | 128/327 |

FOREIGN PATENTS OR APPLICATIONS

| | | | |
|---|---|---|---|
| 39,331 | 3/1907 | Switzerland | 128/169 |
| 122,370 | 7/1901 | Germany | 128/169 |
| 523,142 | 4/1931 | Germany | 128/169 |
| 422,317 | 6/1947 | Italy | 128/169 |

Primary Examiner—Lawrence W. Trapp
Attorney, Agent, or Firm—Arthur T. Fattibene

[57] ABSTRACT

An athletic wrap adapted to encircle a portion of one's body to provide support therefor comprising a wrap portion sufficiently long to encircle the body portion to be wrapped at least once, and having an intermediate elastic portion whereby the tightness of the wrap in the encircling position can be adjusted. Releasable fastening means are provided to secure the wrap in the adjusted encircled position quickly and easily. A tongue is also provided to facilitate the holding of one end of the wrap in initiating the wrapping of the wrap about a portion of the body.

18 Claims, 12 Drawing Figures

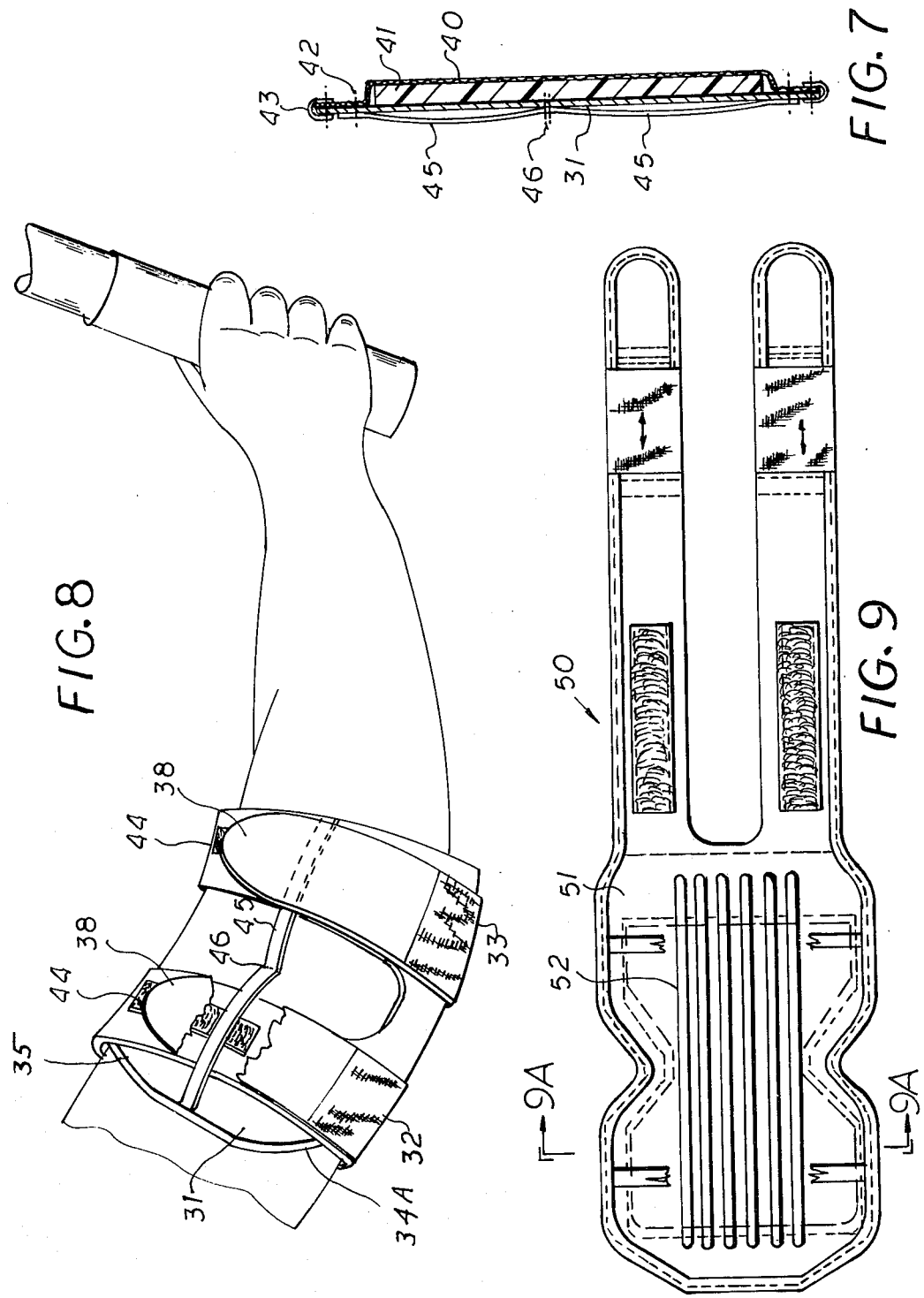

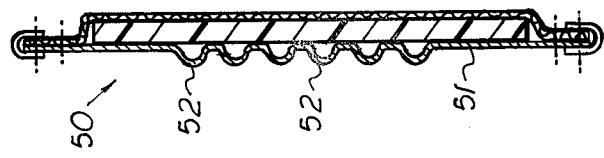
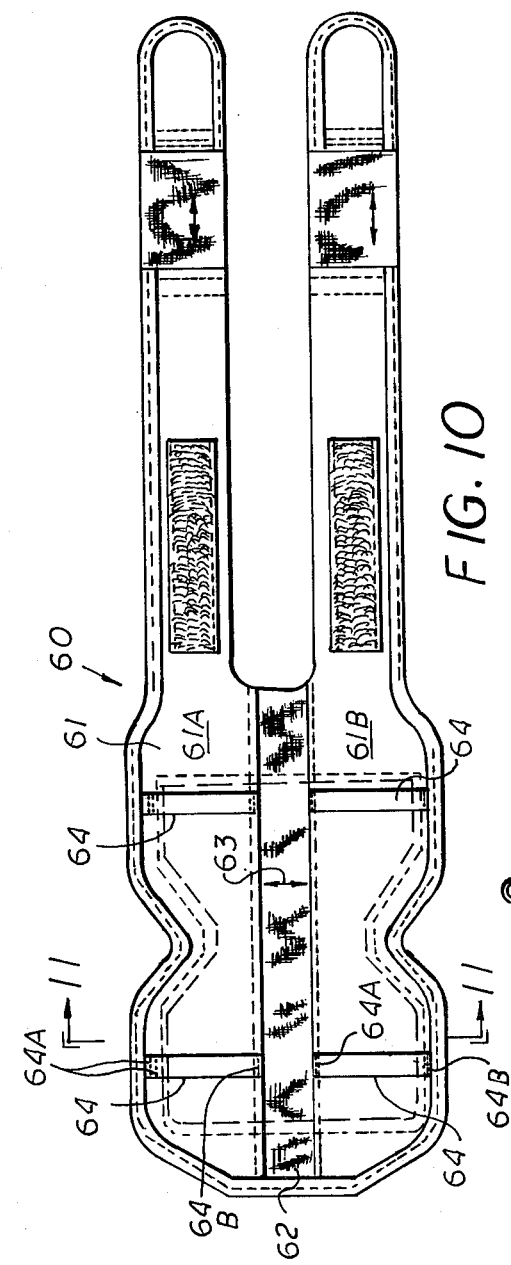
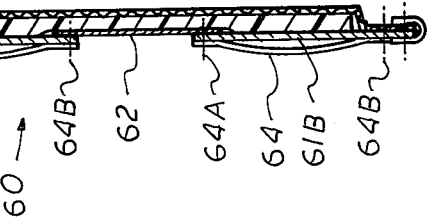

ATHLETIC WRAP

PROBLEM & PRIOR ART

Heretofore, various types of athletic wraps and bands have been used by athlete to reinforce or strengthen such portions of the body as wrists, forearms, legs, etc. Genrally, such wraps comprised simply of an elastic band or wrap or an endless tubular elastic band fitted to the wrist, legs, forearms, etc. It has been noted that such elastic wraps quickly stretch so that their usefulness is short lived. Also with the known wraps which were required to be encircled one or more times about the wrist, etc., difficulty was encountered in initiating the wrap. This was because the free end of the wrap could not be sufficiently held in place until it was overlapped. For this reason, it was generally difficult to apply a band or wrap with the tightness desired.

In certain sports, e.g., tennis, it frequently happens that due to strain or stress of the forearm tendons at the elbow, a player may develop what is normally called a "tennis elbow." While such types of strain is prevalent in tennis, it may occure in other sports as well. When a player has acquired "tennis elbow" symtoms, severe elbow pain occurs when the arm, wrist or hand is used. Under such conditions a player is normally incapable of participating in the game. Treatments for such symptoms generally include medication ,e.g., cortisone treatment, injections, and long periods of rest.

OBJECTS

An object of this invention is to provide an athletic wrap which will relieve and/or prevent stress and strain on a joint during the play of a given sport.

Another object of this invention is to provide an athletic wrap which can be readily applied simply and quickly, and whereby the tightness of the wrap can be readily adjusted to suit the individual.

Another object is to provide a wrap which is capable of providing a firm support, and which will not distort or become misshaped with use.

Another object is to provide an athletic wrap whereby the end is formed so that it can be readily held in initiating the encircling of the wrap about one's wrist, legs, forearms, etc.

Another object is to provide an athletic wrap which is particularly adapted for use to relieve the stress and strain of a "tennis elbow."

Another object is to provide an improved athletic wrap for use on joints such as elbows and knees.

Another object is to provide a wrap for a joint, such as an elbow which provides for firm support without hampering the joint movement.

Another object is to provide a joint support wherein the degree of tightness can be readily adjustable to one's comfort.

BRIEF SUMMARY OF THE INVENTION

The foregoing objects and other features and advantages are attained by an athletic band or wrap adapted to encircle a portion of the body. The wrap includes a wrap portion arranged to encircle a portion of the body and which has a laterally projecting tongue portion adjacent one end to facilitate holding the one end of the wrap to initiate the wrapping operation. An intermediate elastic or stretch portion connects a pull end portion to the wrap portion; and a readily releasably fastening means is provided to maintain the wrap in the encircled position.

In another form of the invention, the wrap is constructed so as to be readily applied to a flexible body joint, e.g, elbow or knee. The construction of the athletic wrap for use as a joint wrap comprises a wrap portion which has a reduced section intermediate thereof and which includes a pair of pull straps whereby the tightness of the wrap can be adjusted on opposite sides of the "joint bend." Each of the respective pull straps include an intermediate elastic portion whereby the tension or tightness of the wrap can be readily adjusted. Releaseable fastening means secure the straps in the adjusted position. A tongue is extended from one end of the wrap to eliminate "pinching" when the wrap is in use. In a modified construction of this embodiment, one or more accordian folds or pleats or an elastic stretch band may be formed in the wrap portion to increase flexibility of the wrap when the joint is bent.

FEATURES

A feature of this invention resides in the provision of an athletic wrap having a lateral projecting tongue which facilitates the holding of one end during a wrapping operation whereby a firm wrap is assured.

Another feature resides in an improved wrap construction which provides firm support for the enwrapped body portion.

Another feature of the invention resides in a joint wrap which can be readily applied to a "flexing joint" in a manner whereby the joint can be relieved of any stress or strain thereon without adversely interfering with its mobility or use.

Other features and advantages will become more readily apparent when considered in view of the drawings and specification in which:

FIG. 7 is a sectional view taken along line 7—7 on FIG. 6.

FIG. 8 is a perspective view showing the application of the wrap of FIGS. 5 thorough 7 as applied to an elbow.

FIG. 9 illustrates a plan view of a modified form of the invention of FIG. 5. FIG. 9A is a section taken along line 9A—9A on FIG. 9.

FIG. 10 is a plan view of another modified wrap construction.

FIG. 11 is a sectional view taken along line 11—11 on FIG. 10.

DETAILED DESCRIPTION

Figure 1:
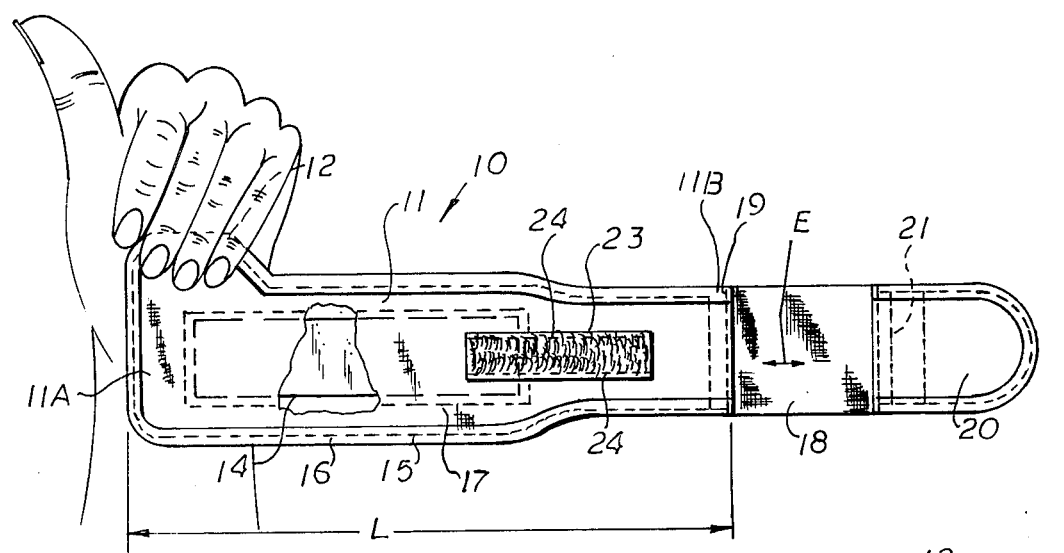
FIG. 1 is a top plan view illustrating the manner in which the wrap is applied to a wrist.
Figure 2:
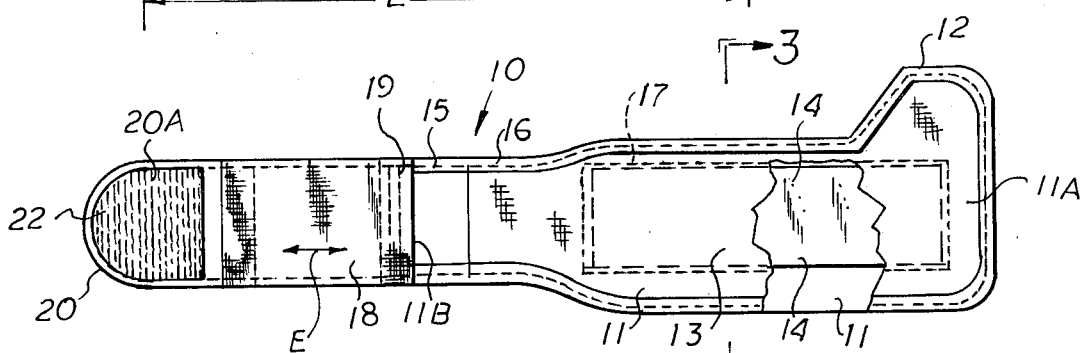
FIG. 2 is a back plan view of the wrap.
Figure 3:
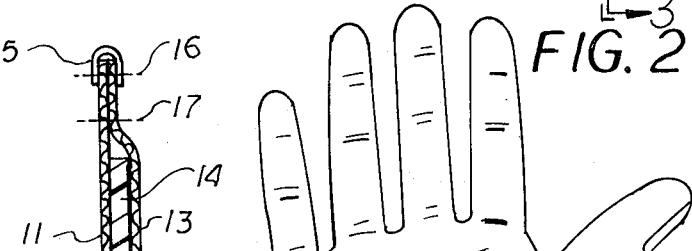
FIG. 3 is a sectional view taken along line 3—3 on FIG. 2.

Referring to the drawings there is shown in FIGS. 1 and 2 an athletic wrap 10 embodying the present invention. While the wrap 10 is illustrated and described as a wrist wrap, it will be readily understood that the wrap 10 can be also utilized for use about other parts of the body, e.g., ankles, forearms, legs, chest, waist, etc. In such other applications, the proportions and/or length of the wrap 10 may vary, but the mode of operation and construction will be the same.

As shown, the wrap 10 comprises a wrap portion 11 which is preferably formed of an non-stretchable material, e.g., sheet plastic, or fabric capable of providing a firm support for the wrapped body portion, e.g., the wrist. The wrap portion 11 is provided with a length L which is sufficiently long so as to encircle the body part at least one time. Adjacent one end 11A of the wrap portion 11, there is formed a laterally projecting tongue 12. As best seen in FIG. 1, the projecting tongue 12 provides a means whereby the person may hold the wrap 10 in place with the fingers of the hand when initiating the wrapping of the wrap 10 about the wrist. By holding end 11A firmly in place during the initiating of the encircling of the wrap 10 until the end 11A has been overlapped, a firm wrap is assured.

Connected to the under or back side of the wrap portion 11 there is provided a suitable liner 13. The inner line 13 may be formed of a suitable soft material, e.g., a flannel or perspiration absorbing material. Disposed between the liner 13 and the wrap portion 11, a resilent pad 14 may be provided for added comfort or support. The pad 14 may be a sheet of foam rubber, plastic or other soft cushion type material. An edge binding 15 circumscribes the marginal edge of the wrap portion 11 and associated liner 13 to provide a finished and neat appearance. It will be noted that the the edge binder 15 is secured by a sewn seam 16. If desired, the pad may be held in place between the liner 13 and wrap portion 11 by a sewn seam 17 which circumscribes the pad 14.

Connected to end 11B of the wrap portion 11 is an intermediate length of a stretchable elastic material 18. The elastic material is made stretchable along a longitudinal axis E. As shown the elastic material or strip 18 is connected to end 11B by a sewn seam 19.

Connected to the free end of elastic strip 18 by a sewn seam 21 is a pull end portion 20. The pull end portion is preferably, not necessarily, formed of the same material as the wrap portion 11. Secured to the under side 20A of the pull end portion 20 is a "Velcro" type hook pile material or fabric 22. As will be hereinafter described, the hook pilematerial 22 is one element of a releaseable fastener by which the wrap 10 may be secured in the "wrapped" or "encircled position."

Connected to the top side of the wrap portion 11 is a strip of a "Velcro" loop pile material 23 which is secured by opposed sewn seams 24—24. Thus in the wrapped position, it will be noted that the "hook pile" 22 connected to the under side 20A of the pull end portion 20 will overly a portion of the "loop pile" strip 23 to define a readily releasable fastening means. See FIG. 4.

In operation the wrap 10 described can be readily applied to a wrist, for example, by the wearer placing the tongue end 12 of the wrap along the inner portion of the wrist whereby the fingers can readily hold the tongue 12 in place. The pull end is then grasped with the other hand whereby the wrap can be readily wound about the wrist. Once the wrap has overlapped the end 11A, and the pull end press fitted in overlying relationship with strip 23 to secure the pull end portion, the tongue 12 can be released. By controlling the degree of stretch of the elastic strip 18 or "pull" on the pull end portion, the degree of tightness of the encircled wrap about the wrist can be readily adjusted to suit the wearer.

Figure 4:
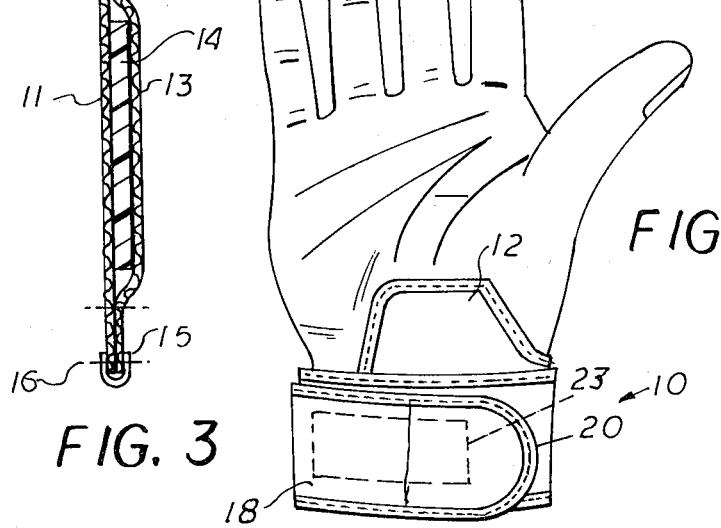
FIG. 4 is a view illustrating the wrap in the operable encircled position about one's wrist.

In the operative position of the wrap 10, as seen in FIG. 4, the projecting tongue 22 can be folded or tucked under the encircled wrap portion if desired.

FIGS. 5 through 8 illustrates a modified form of the invention. In this form of the invention the wrap 30 is constructed for application about a "flexing joint" such as an elbow or knee. Wrap 30 comprises a wrap portion 31 having alength L sufficient to enwrap the "joint", e.g., the elbow at least once. Extending from one end of the wrap portion 31 are a pair of spaced apart pull or wrapping straps 32, 33. In the illustrated form of the invention, the wrap portion 31 and connected straps 32 and 33 are formed of a unitary non-elastic material, e.g., sheet plastic or fabric; leather and the like. Connected to the other end of the wrap portion 31 is a tongue 34. Intermediate the length L of the wrap portion, there is provided with opposed notch or cut-out portions 35—35 to define a restriction at an intermediate point. The notched out portion, when the wrap 30 is placed in use, are positioned either to be on the outside or inside portion of the joint so that flexing of the joint is not impaired.

Figure 5:
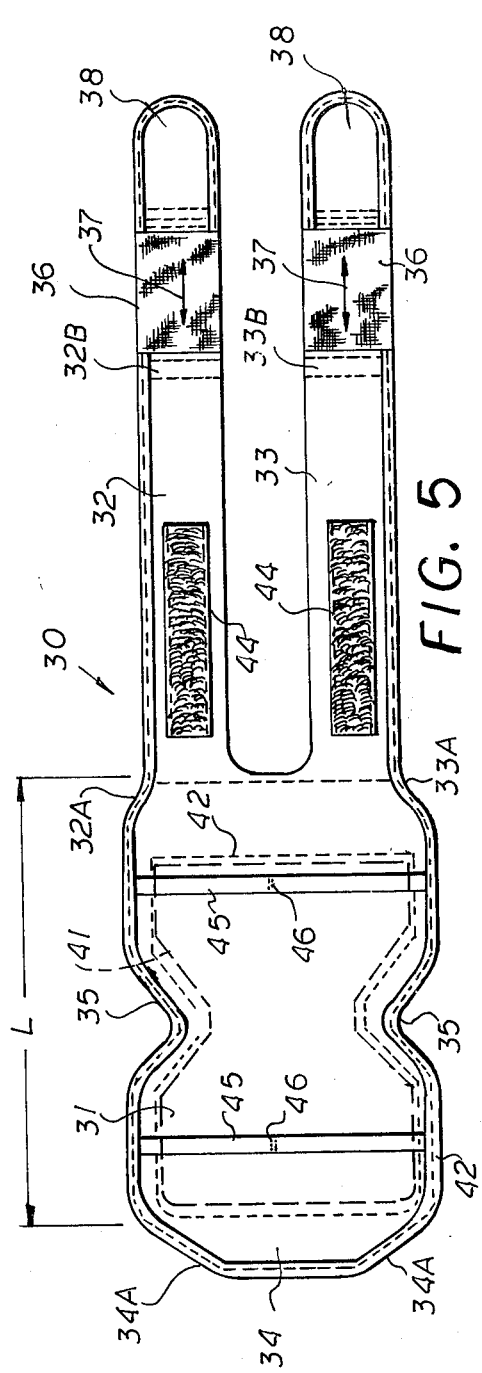
FIG. 5 is a top plan view of a joint wrap embodying the present invention.
Figure 6:
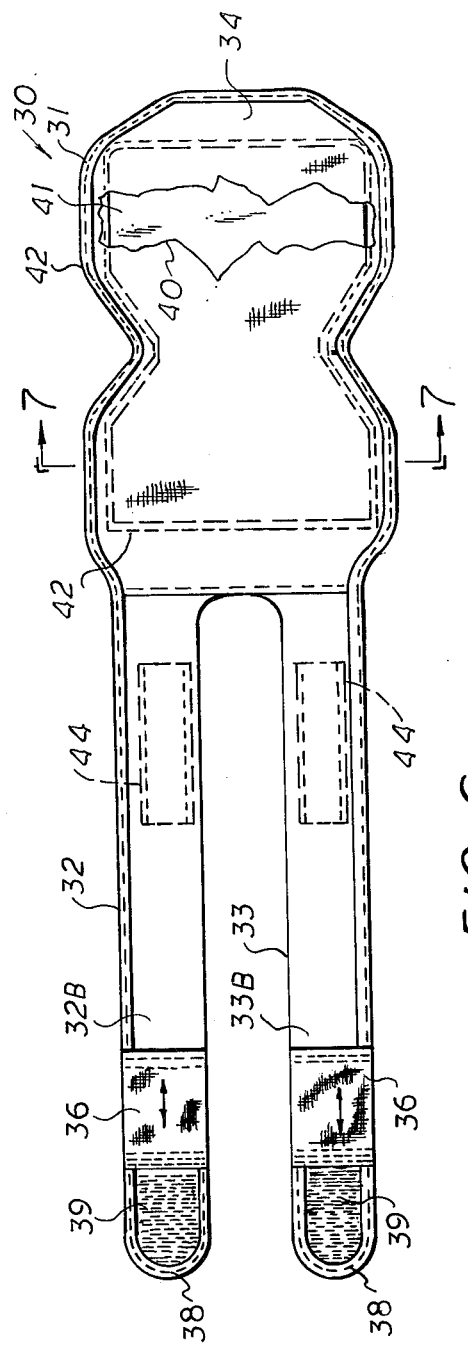
FIG. 6 is a bottom or under side plan view of the wrap of FIG. 5.

As best seen in FIGS. 5 and 6, the tongue portion 34 is provided with a tapering edge 34A. Also the straps 32, 33 at the point 32A, 33A where they extend from the wrap portion 31 are offset inwardly so that in the enwrapped position as shown in FIG. 8, edges 32A, 34A define a "notch" arrangement similar to notch out portion 35, 35 disposed opposite thereto. Thus in the wrapped or encircled position as shown in FIG. 8, the opposed notches 35, 35 and notches defined by 32A, 34A are respectively disposed to the inside and outside of the "joint" so as to not inhibit the flexing thereof.

Connected to ends 32B and 33B of straps 32, 33 is an intermediate elastic strip 36 formed of a suitable elastic or stretch material 36. As shown elastic strip 36 is stretchable longitudinally as indicated by arrows 37.

Connected to the free end of the elastic strip 36 is a pull end tab 38. The underside portion of the pull end tab has connected thereto a "Velcro" hook type of pile 39 which will function as a releaseable fastener similar to that hereinbefore described with respect to FIGS. 1 to 4.

Sewn to the inside portion of the wrap portion is a liner 40 of a soft felt or flannel type material. Disposed between the liner 40 and wrap portion 31 is a flat resilient pad 41 formed of a cushion type material, e.g., foam rubber, sponge or plastic. The pad 41 is held in position between the liner 40 and wrap portion 31 by a circumscribing sewn seam 42. If desired a binder 42 may be swen around the marginal edges of the wrap portion to provide a finished appearance.

Connected to the outer or back side of straps 32, 33 is a strip of a "Velcro" loop pile material 44. The loop pile strip 44 complements the "hook" pile material 39 to define therewith a releaseable fastener. As best seen in FIG. 8, the pull tab 38 is disposed in overlying relationship with strips 44 to secure the straps 32, 33 in the operative position.

If desired, a loop strip 45 may be connected to the back side of the wrap portion 31 to define a loop through which the straps project so as to form a guide for the straps 32, 33. Two such loop straps are shown which are tack sewn at 46 to define two aligned pairs of loops through which straps 32, 33 are threaded.

In the wrapped position as shown in FIG. 8, the tongue portion 34 is disposed to the inside of the joint and function to avoid any "pinching" which may occur when the joint is flexed or bent during the play of a game.

FIG. 9 is a wrap 50 which is similar to the form of the invention described with respect to FIGS. 5 to 8 with the exception that the wrap portion 51 is provided with one or more accordian pleats or folds 52. As shown the pleats are extended in a longitudinal direction. The arrangement is such that when the wrap of FIG. 9 is applied to the joint, the folds 52 will enhance the flexibility of the wrap during joint flexing. In all other respects the contruction of wrap 51 is similar to that described with respect to FIGS. 5 and 6.

With the construction of FIGS. 5 to 9, it will be noted that the wrap can be readily applied to the joint, e.g., the elbow, so that notches 35 are opposite to the notches defined by edges 34A and 32A. With the wrap portion overlapped, the respective straps 32, 33 are threaded through the external loops 45. By pulling on the end tabs 38 the tightness of the wrap can be adjusted due to the action of the elastic strip 36. The elongation or tension imparted by the elastic strip 36 is maintained by securing the end tab 38 to the complemental strip 44. Each strap 32, 33 can be individually adjusted. As the wrap portion 31 is formed for the most part of an non-elastic material, a firm support is imparted to the joint. With the construction described, a firm support is provided without inhibiting the flexibility of the joint.

FIGS. 10 and 11 illustrate a modified wrap construction 60 which is similar to the wrap construction 10 and 50, except that another means is utilized to impart additional flexibility to the wrap 60. As best seen in FIGS. 10 and 11, the wrap portion 61 is defined by two similar sections 61A and 61B which are connected, e.g., by a sewn seam to a strip of an elastic band material 62. It will be noted that the elastic band 62 is stretchable in the direction indicated by arrow 63. As shown, the elastic band 62 extends longitudinally of the wrap portion 61, and it is substantially co-extensive the length thereof. In this form of the invention, the loops 64, which define the strap guides, may be tack stitched to the respective wrap sections 64A and 64B. In all other respects, the wrap construction 60 is similar to that described with respect to FIGS. 5 and 6.

In operation, the wrap construction of FIGS. 10 and 11 is applied to the joint, e.g., the elbow in a manner hereinbefore described. However, because of the elastic band 62 extending longitudinally of the wrap portion 61, additonal flexibility is imparted to the wrap when it is encircled about a joint. This is apparent when it is noted that the elastic band 62 is located at the point where maximum bending radius is required when the joint is flexed.

While the invention has been described with respect to several embodiments thereof, it will be readily understood and appreciated that variations and modifications can be made without departing from the spirit and scope of the invention.

What is claimed is:

1. An athletic wrap comprising:
   a wrap portion adapted to encircle the portion of the body at least once,
   a tongue connected to said wrap portion adjacent one end thereof to facilitate the holding of said one end during a wrapping operation,
   said tongue projecting to one side of said wrap portion,
   a pull end portion,
   an elastic intermediate portion interconnecting said pull end portion to said wrap portion,
   and complementary readily releaseable fastening means in said wrap portion and said pull end portion for releaseably securing said wrap in the encircled position thereof.

2. The invention as defined in claim 1 wherein said wrap portion includes a resilient pad connected thereto,
   said pad being disposed adjacent to the body in the encircling position of said wrap.

3. The invention as defined in claim 1 wherein said wrap portion is formed of a generally non-elastic material.

4. The invention as defined in claim 3 and including an inner liner co-extensive of said wrap portion to confine said pad between said non-elastic material and said liner.

5. The invention as defined in claim 1 wherein said fastening means includes a strip of pile material connected to said wrap portion, and releaseable fiber hooks connected to said pull end portion whereby in the encircled position of said wrap, said fiberous hooks of said pull end portion overly and engages to pile strip.

6. The invention as defined in claim 1 wherein said tongue projects laterally of said wrap portion.

7. An athletic wrist band comprising:
   a wrap portion formed of a firm non-elastic material,
   a laterally extending tongue connected adjacent one end of said wrap portion,
   said tongue defining a holding portion for initiating the wrapping of said wrap portion about the wrist, and
   said wrap portion being sufficiently long so as to encircle the wrist at least once,
   an inner liner connected to said wrap portion,
   a resilient pad disposed between said liner and said wrap material,
   an intermediate elastic portion connected to the other end of said wrap portion,
   a pull end portion connected to the free end of said elastic portion,
   a readily releasable fastening means for releaseably securing said wrap in the encircled position about said wrist,
   said fastening means including a pile strip connected to the back side of said wrap portion, and complementary fiberous hook means connected to the inner side of said pull end portion.

8. The invention as defined in claim 7 wherein said elastic portion is stretchable in the longitudinal direction for adjusting the tightness of the wrap in the encircled position thereof.

9. An athletic wrap comprising:
   a wrap portion having a connected tongue adjacent one end thereof,
   a pull strap connected to the other end of said wrap portion to form an extension thereof,
   said pull strap including an intermediate stretchable elastic segment,
   said wrap portion being adapted to enwrap a portion of a body,
   sand said pull strap encircling said wrap portion in the operative position thereof, and a readily releaseable fastening means for securing said pull strap in the operative position of said wrap.

10. The invention as defined in claim 9 wherein said wrap portion is sufficiently long to overly the tongue portion in the enwrapped position.

11. The invention as defined in claim 9 wherein a resilient pad is included connected to the underside of said wrap portion.

12. The invention as defined in claim 9 and including an accordian fold extending longitudinally of said wrap portion.

13. The invention as defined in claim 9 wherein said wrap portion is formed with opposed notches to define a restricted portion intermediate the length thereof.

14. The invention as defined in claim 13 and including means connected to the opposed ends of said wrap portion which in the enwrapped position of said wrap defines a notch configuration oppositely disposed to said opposed notches.

15. An athletic wrap for relieving stress and strain on a flexible joint comprising:
    a wrap portion having a tongue portion connected to one end thereof, and a pair of spaced apart straps connected to the other end thereof,
    said wrap portion having opposed notches formed intermediate the ends thereof to define a restricted intermediate portion,
    said tongue in the enwrapped position of said wrap being disposed opposite to said opposed notches,
    an intermediate elastic strip connected to each of said straps,
    a pull tab connected to the end of each said elastic strip,
    a releaseable fastener for securing said straps in the enwrapped position,
    said releaseable fastener including a hook type pile connected to said pull tab,
    and a complemental loop type pile connected to each of said straps so that in the enwrapped position said hook type pile pressed onto said loop type pile releaseably secures said strap in the enwrapped position,
    a liner connected to said wrap portion,
    and a resilient pad disposed between said liner and wrap portion.

16. The invention as defined in claim 15 and including means defining loops formed on said wrap portion through which said straps are guided in the enwrapped position.

17. The invention as defined in claim 15 and including a series of accordian folds extending longitudinally of said wrap portion.

18. The invention as defined in claim 9 and including elastic band disposed intermediate the width of said wrap portion, and
    said elastic band extending longitudinally of said wrap portion,
    said elastic band being stretchable in a direction normal to the length thereof.

* * * * *